(12) United States Patent
Fei et al.

(10) Patent No.: US 8,989,462 B2
(45) Date of Patent: Mar. 24, 2015

(54) SYSTEMS, METHODS AND COMPUTER READABLE STORAGE MEDIUMS STORING INSTRUCTIONS FOR APPLYING MULTISCALE BILATERAL FILTERING TO MAGNETIC RESONANCE (RI) IMAGES

(75) Inventors: Baowei Fei, Dunwoody, GA (US); Xiaofeng Yang, Atlanta, GA (US)

(73) Assignee: Emory University, Atlanta, GA (US)

( * ) Notice: Subject to any disclaimer, the term of this patent is extended or adjusted under 35 U.S.C. 154(b) by 246 days.

(21) Appl. No.: 13/522,646

(22) PCT Filed: Feb. 11, 2011

(86) PCT No.: PCT/US2011/024565
§ 371 (c)(1),
(2), (4) Date: Aug. 8, 2012

(87) PCT Pub. No.: WO2011/100575
PCT Pub. Date: Aug. 18, 2011

(65) Prior Publication Data
US 2012/0294503 A1    Nov. 22, 2012

Related U.S. Application Data

(60) Provisional application No. 61/303,392, filed on Feb. 11, 2010.

(51) Int. Cl.
*G06K 9/00* (2006.01)
*G06T 7/00* (2006.01)
*A61B 5/055* (2006.01)

(52) U.S. Cl.
CPC ............. *G06T 7/0081* (2013.01); *G06T 7/0095* (2013.01); *A61B 5/055* (2013.01); *G06T 2207/10088* (2013.01); *G06T 2207/20016* (2013.01); *G06T 2207/20028* (2013.01);
(Continued)

(58) Field of Classification Search
CPC .................. A61B 5/726; G06T 7/0012; G06T 2207/10072; G06T 2207/10081; G06T 2207/10088; G06T 2207/30004; G06T 2207/30016; G06T 2211/421; G06T 11/008; G06T 2207/20048; G06T 2207/20068; G06T 5/10
USPC .................................................. 382/128–134
See application file for complete search history.

(56) References Cited

U.S. PATENT DOCUMENTS

| 4,718,010 A | * | 1/1988 | Fujii | 378/5 |
| 5,841,890 A | * | 11/1998 | Kraske | 382/131 |
| 7,652,259 B2 | | 1/2010 | Kimchy et al. | |

FOREIGN PATENT DOCUMENTS

WO    2008064319 A2    5/2008

OTHER PUBLICATIONS

El Fakhri, et al., (2003), " MRI-Guided SPECT Perfusion Measures and Volumetric MRI in Prodromal Alzheimer Disease.", Archives of Neurology, 60(8): 1066-1072.
(Continued)

*Primary Examiner* — Alex Liew
(74) *Attorney, Agent, or Firm* — Emory Patent Group

(57) ABSTRACT

Systems, methods and computer-readable storage mediums relate to segmenting MR images using multiscale bilateral filtering. Before the multiscale bilateral filtering, the MR images are transformed from the Image Domain to the Radon Domain.

19 Claims, 13 Drawing Sheets

(52) U.S. Cl.
CPC ............ G06T2207/20036 (2013.01); G06T 2207/30016 (2013.01)
USPC ..................................................... 382/128

(56) References Cited

OTHER PUBLICATIONS

Hofmann, et al., (2009), "Towards Quantitative PET/MRI: A Review of MR-Based Attenuation Correction Techniques.", European Journal of Nuclear Medicine and Molecular Imaging, 36(Suppl 1): S93-S104.

Zaidi, et al., (2002), "Fuzzy Clustering-Based Segmented Attenuation Correction in Whole-Body PET Imaging.", Physics in Medicine and Biology, 47(7):1143-1160.

Zaidi, et al., (2004), "Attenuation Compensation in Cerebral 3D PET: Effect of the Attenuation Map on Absolute and Relative Quantitation.", European Journal of Nuclear Medicine and Molecular Imaging, 31(1):52-63.

Zaidi, et al., (2003), "Magnetic Resonance Imaging-Guided Attenuation and Scatter Corrections in Three-Dimensional Brain Positron Emission Tomography.", Medical Physics, 30(5):937-948.

* cited by examiner

| -1 | -3 | -5 | -3 | -1 |
|----|----|----|----|----|
| 0  | 0  | 0  | 0  | 0  |
| 1  | 3  | 5  | 3  | 1  |

(b) 1120:

| 1  | 3  | 5  | 3  | 1  |
|----|----|----|----|----|
| 0  | 0  | 0  | 0  | 0  |
| -1 | -3 | -5 | -3 | -1 |

SYSTEMS, METHODS AND COMPUTER READABLE STORAGE MEDIUMS STORING INSTRUCTIONS FOR APPLYING MULTISCALE BILATERAL FILTERING TO MAGNETIC RESONANCE (RI) IMAGES

CROSS REFERENCE TO RELATED APPLICATIONS

This application is a national stage of International Application PCT/US2011/024565, filed Feb. 11, 2011, which claims priority to U.S. Provisional Application No. 61/303,392, filed Feb. 10, 2010, which applications are hereby incorporated by this reference in their entireties.

BACKGROUND INFORMATION

Magnetic Resonance (MR) images provide invaluable information to medical practitioners. However, due to the presence of imaging artifacts, anatomical variability, varying contrast properties, and poor registration, conventional techniques do not yield satisfactory results over a wide range of scan types and neuroanatomies without manual intervention. Moreover, traditional techniques are not robust enough for large scale analyses.

Thus, there is a need for an image processing technique that is robust and accurate.

SUMMARY

Systems, methods and computer-readable storage mediums storing instructions are provided for segmenting MR images using multiscale bilateral filtering. In some embodiments, a method, performed by a computer having a memory and a processor, for segmenting anatomical landmark in digital medical images, may include: transforming at least one digital image of an anatomical landmark from an Image Domain to a Radon Domain to obtain an original sinogram; decomposing the original sinogram to obtain a plurality of sinograms, each of the plurality of sinograms being at a different scale; combining the plurality of sinograms into a binary sinogram; and reconstructing the binary sinogram into a reconstructed sinogram.

In some embodiments, the method may include transforming the reconstructed sinogram from the Radon Domain to the Image Domain to obtain a segmented MR Image. In further embodiments, the method may include displaying the segmented MR Image. In further embodiments, the method may include using the segmented MR Image for attenuation control of a positron emission tomography (PET) Image. In other embodiments, the decomposing is performed using a bilateral filter.

In some embodiments, the decomposing may include filtering the original sinogram to a scale of six, wherein the plurality of sinograms is six sinograms. In other embodiments, the method may include filtering each of the plurality of sinograms with a gradient filter after the decomposing the sinogram to the plurality of sinograms. In some embodiments, the gradient filter may be selected based on the anatomical landmark. In other embodiments, the anatomical landmark may include any one, or a combination, of a brain, at least one lung, a thorax, and at least one bone.

In further embodiments, the transformation may be based on the following calculation:

$$P_s(\alpha) = Rf(\alpha,s) = \int_{-\infty}^{\infty} \int_{-\infty}^{\infty} f(x,y)\delta(s - x \cos \alpha - y \sin \alpha) dx dy \ \alpha \in [0,\pi] / s \in R.$$

In some embodiments, a computer-readable storage medium may store instructions for segmenting an anatomical landmark in digital medical images, the instructions may include: transforming at least one digital image of an anatomical landmark from an Image Domain to a Radon Domain to obtain an original sinogram; decomposing the original sinogram to obtain a plurality of sinograms, each of the plurality of sinograms being at a different scale; combining the plurality of sinograms into a binary sinogram; and reconstructing the binary sinogram into a reconstructed sinogram.

In some embodiments, the medium may include instructions for transforming the reconstructed sinogram from the Radon Domain to the Image Domain to obtain a segmented MR Image. In further embodiments, the medium may include displaying the segmented MR Image. In further embodiments, the medium may include instructions for using the segmented MR Image for attenuation control of a PET Image. In other embodiments, the decomposing is performed using a bilateral filter.

In some embodiments, a system for processing PET and MR images from a PET/MRI machine may include an apparatus including at least one processor; and at least one memory including computer program code. The at least one memory and the computer program code configured to, with the at least one processor, may cause the apparatus to perform at least the following: transforming at least one digital image of an anatomical landmark from an Image Domain to a Radon Domain to obtain an original sinogram; decomposing the original sinogram to obtain a plurality of sinograms, each of plurality of sinograms being at a different scale; combining the plurality of sinograms into a binary sinogram; and reconstructing the binary sinogram into a reconstructed sinogram.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 11(a) and 11(b) show kernels for two filters for a brain scan according to an exemplary embodiment;

DETAILED DESCRIPTION OF THE EMBODIMENTS

Figure 1:
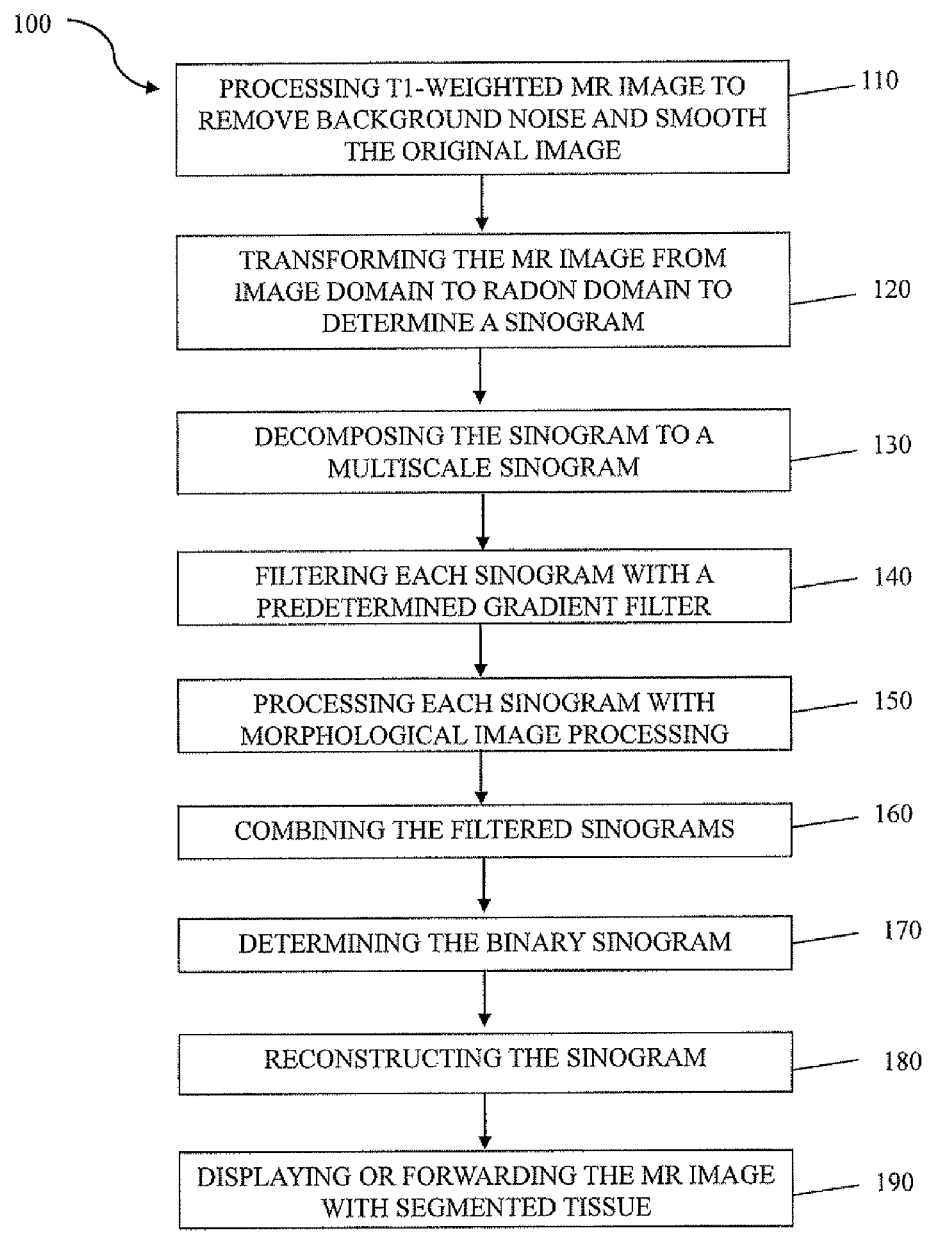
FIG. 1 shows a method according to an exemplary embodiment to obtain a segmented tissue image from a scanned original MR image of a subject's anatomy.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The methods of the disclosure are described with respect to a brain scan. However, it should be understood that the disclosure is not limited to the brain and may be applied to scans of other anatomical landmarks, including but not limited to, scans of a thorax, at least one lung, and at least one bone.

The methods of the disclosure are not limited to the steps described herein. The steps may be individually modified or omitted, as well as additional steps may be added.

Unless stated otherwise as apparent from the following discussion, it will be appreciated that terms such as "decomposing," "filtering," "combining," "reconstructing," "segmenting," "generating," "registering," "determining," "obtaining," "processing," "computing," "selecting," "estimating," "detecting," "tracking," "obtaining" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

Attenuation correction (AC) is an essential step in the study of quantitative PET imaging of certain body anatomy, specifically those having a well-defined outline such as a scalp, thorax, and lung. One approach is to use MR images for attenuation correction of PET images, involving a segmented tissue technique in which a scan for attenuation correction is taken to segment the scanned anatomy to produce an attenuation correction (AC) map.

For example, with respect to a brain scan, the brain may be segmented into the scalp, skull, and brain tissue so that one can assign different attenuation coefficients to the segmented tissue and then produce the AC map. On the AC map, the skull has the largest attenuation coefficient; and thus will dominate the attenuation correction of the image. Once the skull is segmented from MR images, the shape and size of the scalp that is outside of the skull and the brain tissue that is inside of the skull may be determined.

Traditionally, many combined PET/MRI machines do not offer transmission scans for attenuation correction because of space limit considerations. Additionally, as mentioned, a number of techniques that have been proposed to segment tissue in MR images fail to provide satisfactory results over a wide range of scan types and anatomies.

Segmentation Method

FIG. 1 illustrates a method according to an embodiment to obtain a segmented tissue image from a scanned original MR image of a subject's anatomy. In some embodiments, segmentation method 100 may include a preprocessing step 102 that processes T1-weighted MR images. The preprocessing step 102 may include processing T1-weighted MR images using a predetermined threshold and a Gaussian filter in order to remove the background noise and smooth the original image. The preprocessing may be according to methods well known in the art.

Transforming Step

The method 100 may further include a transforming step 104 that transforms the MR image from the Image Domain to the Radon Domain to obtain a sinogram. In some embodiments, the Radon transform may be defined as follows from a complete set of line integrals $P_s(\alpha)$.

$$P_s(\alpha)=Rf(\alpha,s)=\int_{-\infty}^{\infty}\int_{-\infty}^{\infty}f(x,y)\delta(s-x\cos\alpha-y\sin\alpha)dxdy \quad \alpha\in[0,\pi] s\in R. \quad (1)$$

Figure 2:
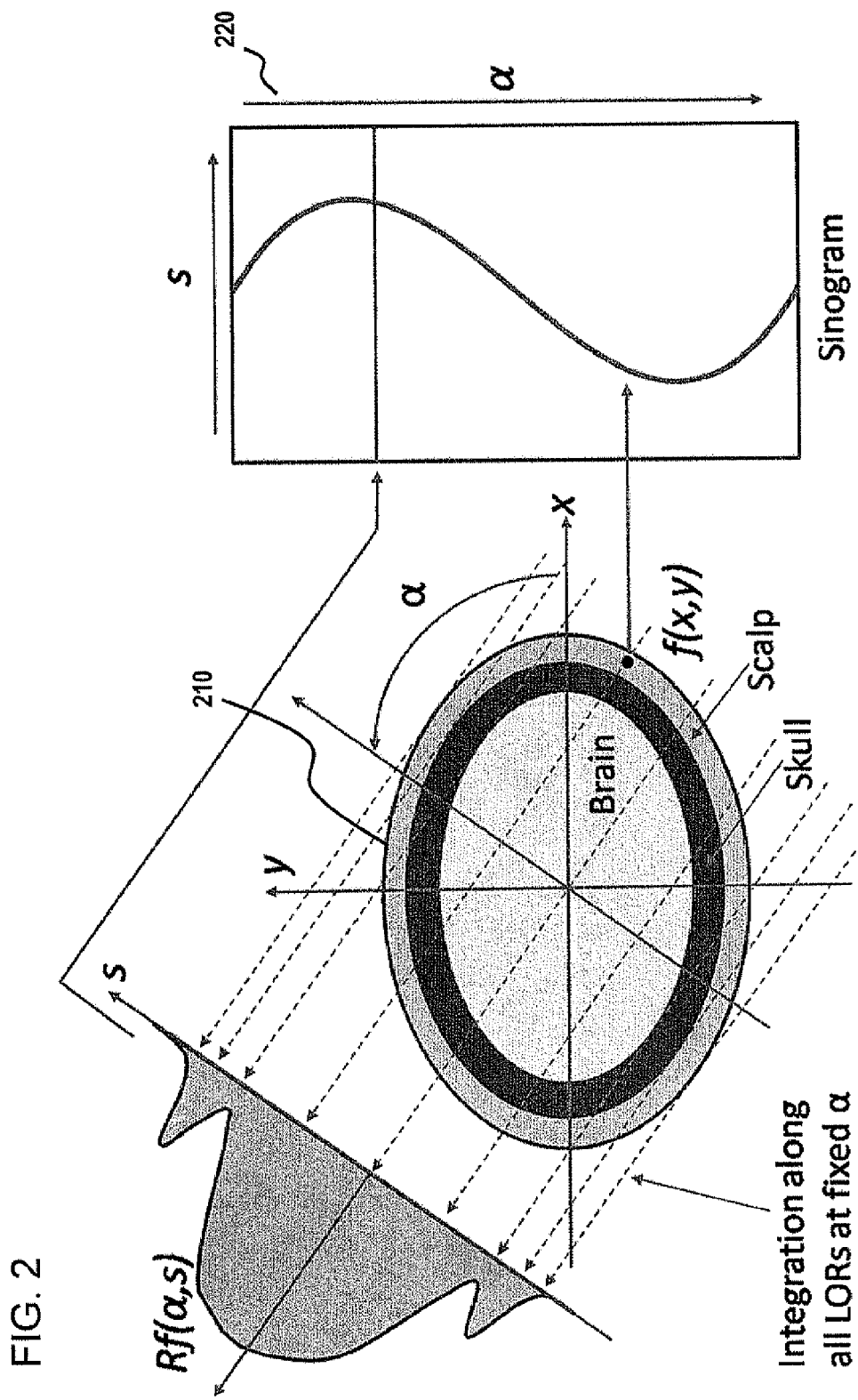
FIG. 2 illustrates an example of a schematic diagram of the Radon transform with respect to a brain scan.

FIG. 2 illustrates an example of a schematic diagram of the Radon transform with respect to a brain scan 210. As shown in FIG. 2, s is the perpendicular distance of a line from the origin and $\alpha$ is the angle formed by the distance vector. In this example, the projection image, i.e., sonogram 220 may have two gaps because of low signal for skull. The point $f(x, y)$ 215 in the brain scan 210 corresponds to the sine curve in the Radon domain. According to the Fourier slice theorem, this transformation is invertible. The Fourier slice theorem states that for a 2-D function $f(x, y)$ 215, the 1-D Fourier transforms of the Radon transform along s, are the 1-D radial samples of the 2-D Fourier transform of $f(x, y)$ 215 at the corresponding angles. This is more fully detailed, for example, in Yang et al., 2010, Proc. SPIE 2010 Mar. 4; 7623, (1):76233K, 7623, 76233K, which is incorporated in its entirety.

Figure 3:
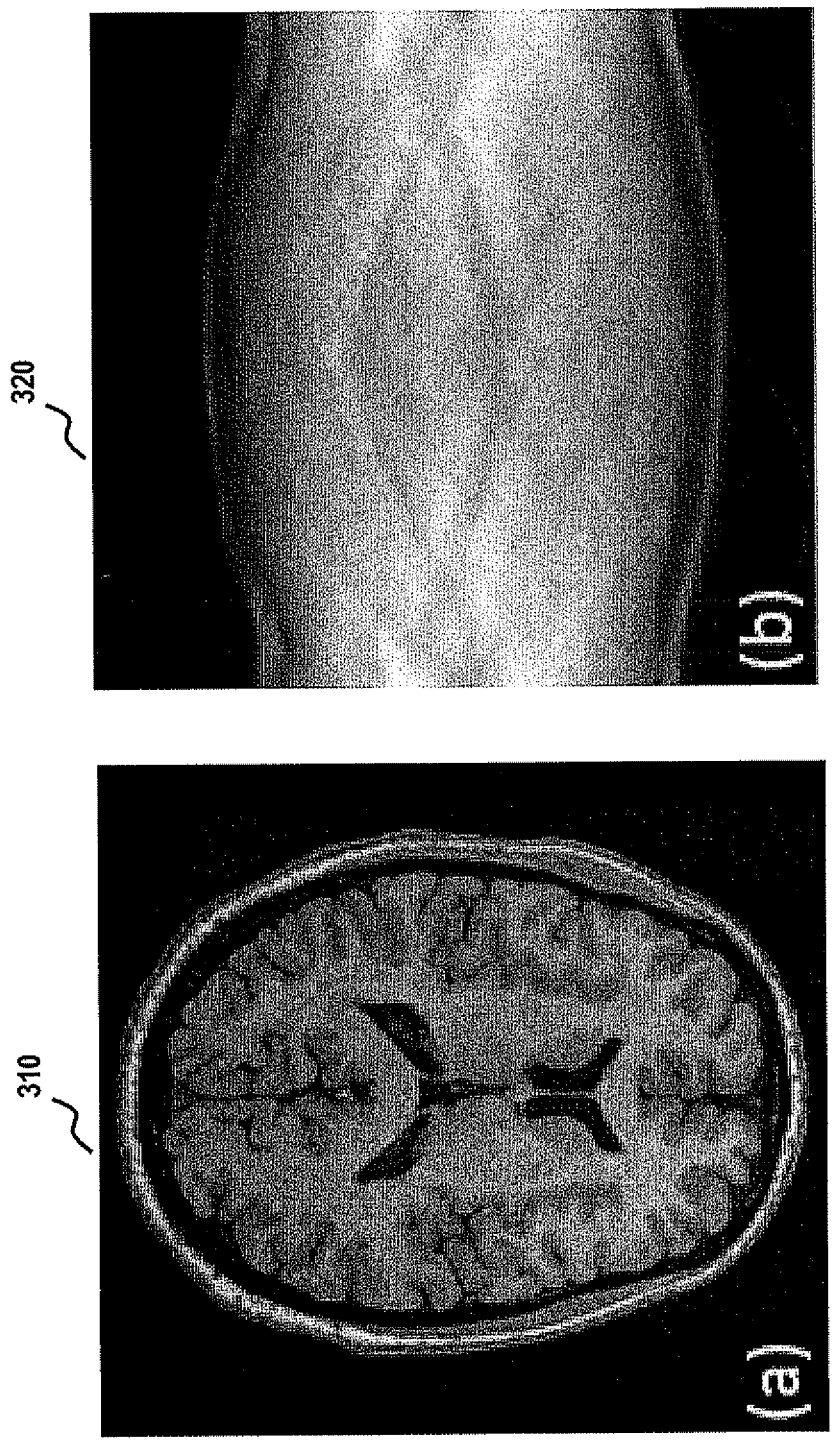
FIGS. 3(a) and 3(b) illustrate an example of a transformation of a MR image of a brain.

FIGS. 3(a) and 3(b) illustrate an example of a transformation of a MR image 310 of a brain. FIG. 3(a) illustrates the MR image 310 and FIG. 3(b) illustrates the corresponding sinogram 320 in the Radon domain. As shown in FIG. 3(b), there may be two low intensity gaps on top and bottom sides of the sinogram 320 along the vertical direction, which indicate the skull may have relatively low signal intensity on the T1-weighted MR image.

Using the Radon Transform according to some embodiments may improve the robustness of the image to noise. Assuming white noise with zero mean is added to the image, the Radon transform of noise will be constant for all of the points and directions and will be equal to the mean value of the noise, which is assumed to be zero, because the Radon transform is line integral of the image, for the continuous case. Accordingly, zero-mean white noise may have no effect on the Radon transform of the image.

Figure 4:
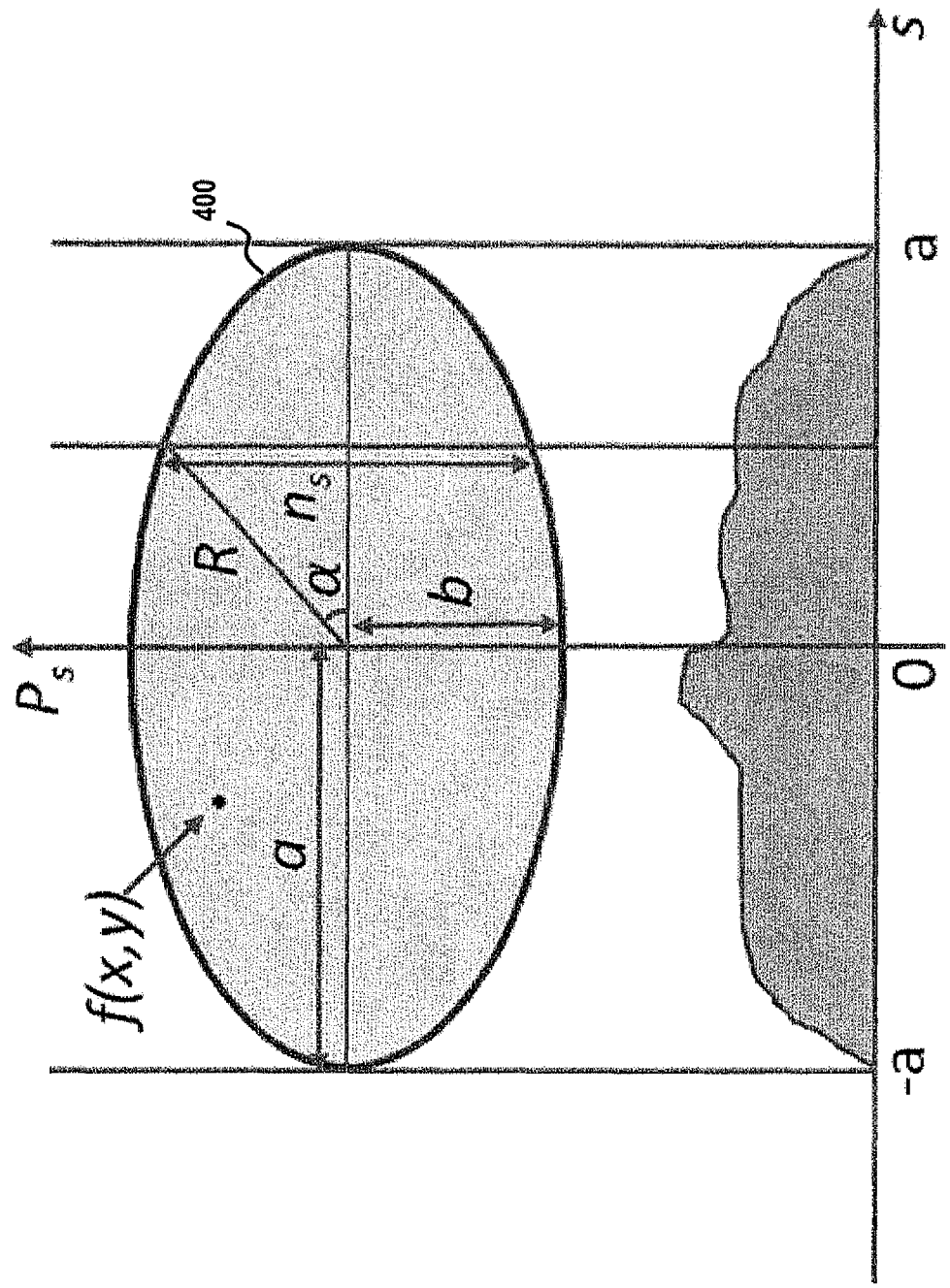
FIG. 4 illustrates an example of how the Radon transform according to embodiments may improve the signal to noise rate (SNR)

FIG. 4 illustrates an example of how the Radon transform according to embodiments may improve the signal to noise rate (SNR). Specifically, FIG. 4 illustrates an example of a brain ellipse model 400 and calculation scheme in the Radon domain. The example may be described by the following equation:

$$\frac{x^2}{a^2} + \frac{y^2}{b^2} = 1 (a \geq b) \tag{2}$$

To demonstrate the improved SNR, the intensity values along the pixels for the Radon transform may be summed as shown in FIG. 4. The following calculations are based on the assumption that the point $f(x, y)$ is 2D discrete signals whose intensity values are independent of random variables with mean $\mu$ and variance $\sigma^2$. For each point along the projection $p_s$, $n_s$ pixels of $f(x, y)$ are summed and therefore, mean $(p_s)=n_s \cdot \mu$ and $\text{var}(p_s)=n_s \cdot \sigma^2$.

Meanwhile, $n_s = s \cdot \tan \theta = R \cdot \sin \theta$ and $R = \alpha b / \sqrt{b^2 \cos^2 \theta + \alpha^2 \sin^2 \theta}$, where R is the radius of the ellipse area in terms of pixels, and the integer s is the projection index, which varies from $-\alpha$ to $\alpha$.

The average of $P_s^2$ is $$A(p_s^2) = \frac{1}{2a} \sum_{s=-a}^{a} p_s^2 \tag{3}$$

Its expected value is defined as $E_p = E\{A(p_s^2)\}$.

$$E_p = \frac{1}{2a} \sum_{s=-a}^{a} E\{p_s^2\} \tag{4}$$

$$= \frac{1}{2a} \sum_{s=-a}^{a} [\text{var}(p_s) + (E(p_s))^2]$$

$$= \frac{1}{2a} \sum_{s=-a}^{a} (n_s \sigma^2 + n_s^2 \mu^2)$$

For large $\alpha$, $$E_p \approx \frac{1}{2a} \int_{-a}^{a} (n_s \sigma^2 + n_s^2 \mu^2) ds \tag{5}$$

$$ds = -\left(\frac{a^3 b \sin \theta}{(b^2 + (a^2 - b^2)\sin^2 \theta)^{3/2}}\right) d\theta$$

where $$E_p = \int_0^\pi \left(\frac{a^3 b \sin \theta}{(b^2 + (a^2 - b^2)\sin^2 \theta)^{3/2}}\right) \cdot \tag{6}$$

$$\left(\frac{\sigma^2 b \sin \theta}{\sqrt{b^2 + (a^2 - b^2)\sin^2 \theta}} + \frac{2\mu^2 ab^2 \sin^2 \theta}{\sqrt{b^2 + (a^2 - b^2)\sin^2 \theta}}\right) d\theta$$

In order to simplify this integral, $\alpha = b$, just like a circular area.

$$E_p = \int_0^\pi (a\sigma^2 \sin^2 \theta + 2\mu^2 \theta^2 \sin^3 \theta) d\theta \tag{7}$$

$$E_p = a\sigma^2 \left(\frac{\theta}{2} - \frac{\sin \theta}{4}\right)\Big|_0^\pi + 2\mu^2 a^2 \left(\frac{1}{12}(\cos(3\theta) - 9\cos \theta)\right)\Big|_0^\pi \tag{8}$$

$$= \frac{\pi a}{2} \sigma^2 + \frac{8}{3} \mu^2 a^2$$

Thus for the signal, $$E_s \approx \frac{\pi a}{2} \sigma_s^2 + \frac{8}{3} \mu_s^2 a^2.$$

And for Gaussian white noise with zero mean and variance $\sigma_n^2$, $$E_n \approx \frac{\pi a}{2} \sigma_n^2.$$

Thus $\text{SNR}_{Radon}$ in Radon domain may be calculated as $$SNR_{Radon} = \frac{E_s}{E_n} = \frac{\sigma_s^2}{\sigma_n^2} + \frac{16a}{3\pi} \cdot \frac{\mu_s^2}{\sigma_n^2} \tag{9}$$

In the original MR image, the $\text{SNR}_{MRI}$ may be defined as $\text{SNR}_{MRI} = (\sigma_s^2 + \mu_s^2)/\sigma_n^2$. So $$SNR_{Radon} = \frac{\sigma_s^2 + \mu_s^2}{\sigma_n^2} + \left(\frac{16a}{3\pi} - 1\right) \cdot \frac{\mu_s^2}{\sigma_n^2} \tag{10}$$

$$= SNR_{MRI} + \left(\frac{16a}{3\pi} - 1\right) \cdot \frac{\mu_s^2}{\sigma_n^2}$$

In practice, for real brain MRI, generally, $\mu_s^2 \geq \sigma_s^2$. So $$SNR_{MRI} = (\sigma_s^2 + \mu_s^2)/\sigma_n^2 \leq 2\mu_s^2/\sigma_n^2 \tag{11}$$

$$SNR_{Radon} \geq \left(\frac{8a}{3\pi} + \frac{1}{2}\right) SNR_{MRI} = \frac{16a + 3\pi}{6\pi} SNR_{MRI} \tag{12}$$

Thus, these calculations may demonstrate that $\text{SNR}_{Radon}$ may be at least increased by a factor of $$\frac{16a + 3\pi}{6\pi}.$$

If the size of MR image is 256*256, thus $$SNR_{Radon} \geq \frac{16 \times 256 + 3\pi}{6\pi} \approx 218.$$

So the SNR has been increased by $10 \log_{10}(218) \approx 23.4$ dB. As a result, this method may be robust to additive noise.

Figure 5:
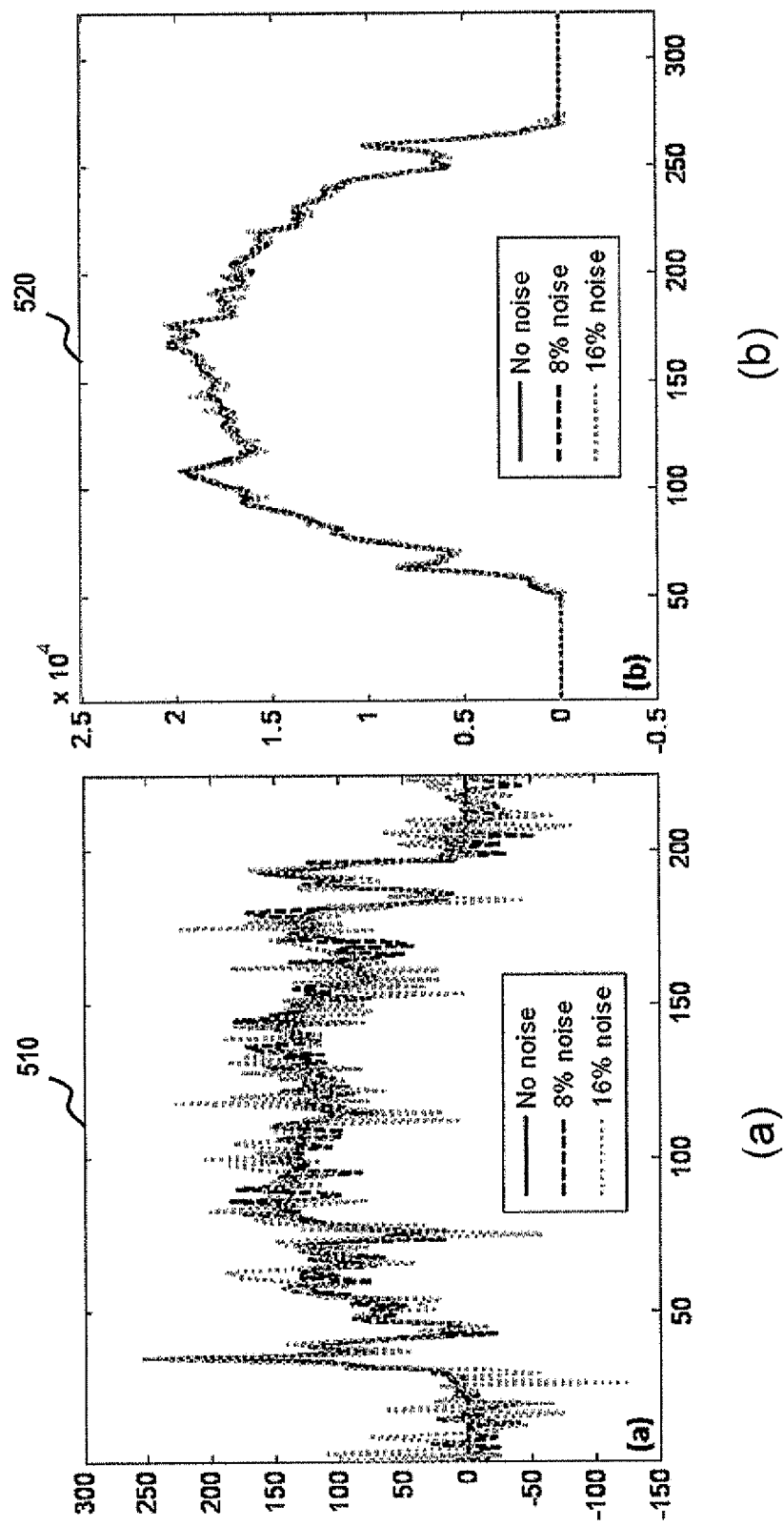
FIGS. 5(a) and (b) illustrate an example of how the Radon transform may decrease the noise in the original images by illustrate the profiles drawing through MR images and corresponding sinograms, respectively.

FIGS. 5(a) and (b) illustrate an example of how the Radon transform may decrease the noise in the original images by illustrate the profiles drawing through MR images and corresponding sinograms, respectively. A first comparison of line profiles 510 is illustrated in FIG. 5(a), in which 8% and 16% noise were added to the original MR image. As shown, the image with 16% noise has severe contamination as the details were lost on the noised image. However, as illustrated in a second comparison of profiles 520 in FIG. 5(b), the profiles between the corresponding sinograms are close, showing that the Radon transform has decreased the noise in the original images. Before the Radon transform, the SNRs are 28.2 dB and 14.4 dB for 8% and 16% noised image, respectively. After the Radon transform, the SNRs are 63.8 dB and 50.1 dB, respectively. Thus, the SNRs are increased by 35.6 dB and 35.7 dB.

Decomposing Step

The method may further include step 130 that decomposes the sinogram to a multi-scale sinogram. In some embodiments, the decomposing step 130 may performed by the steps shown in FIG. 6. The decomposing method may result in a multiscale sinogram representing a series of images with different levels of spatial resolution. In the course scale, the general information is extracted and maintained in images, and in the fine scale, images have more local tissue information.

Figure 6:
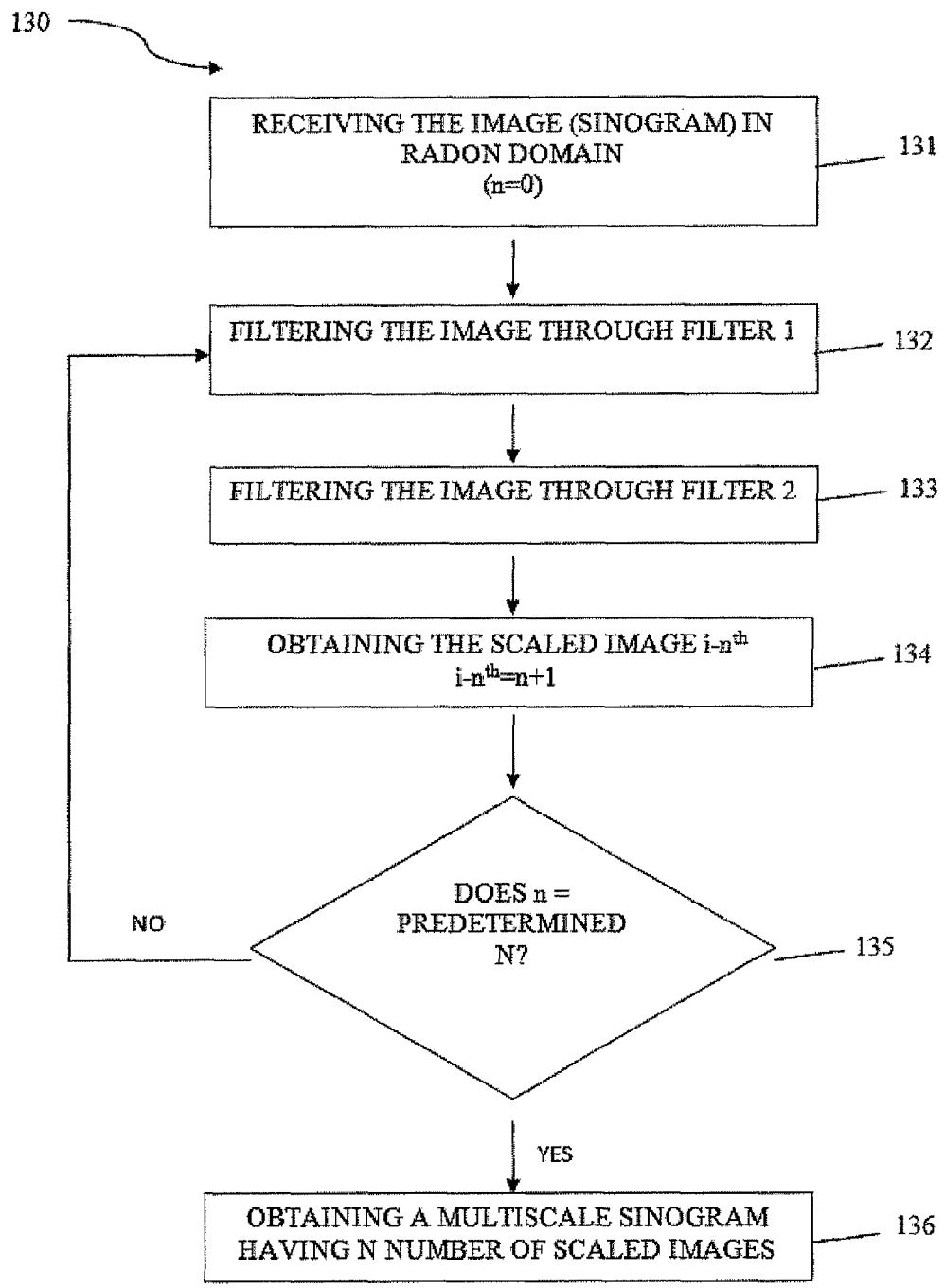
FIG. 6 shows a method of decomposing an original sinogram to a multi-scale sinogram according to an exemplary embodiment.

As shown in FIG. 6, the decomposing step 130 may include a receiving step 131 for receiving the image in the Radon domain. Because the image is original, the scale, i, equals 0.

In some embodiments, the decomposing may be performed by a bilateral filter by a factor of 2. As shown in FIG. 6, the decomposing step may further include two filtering steps 132 and 133.

Bilateral filtering is a non-linear filtering technique. Such technique is further detailed in Tomasi and Manduchi, 1998, Computer Vision, 1998, Sixth International Conference, 839-846, which is incorporated by reference in its entirety. In some embodiments, the filter may be a weighted average of the local neighborhood samples, where the weights are computed based on temporal (or spatial in case on images) and radiometric distance between the center sample and the neighboring samples. The bilateral filtering may smooth the images while preserving edges, by means of a nonlinear combination of nearby image values. Bilateral filtering may be described as follows:

$$h(x) = \lambda^{-1}(x) \int_{-\infty}^{\infty}\int_{-\infty}^{\infty} I(\xi)W_{\sigma_s}(\xi-x)W_{\sigma_r}(I(\xi)-I(x))d\xi \quad (13)$$

with the normalization that ensures that the weights for all the pixels add up to one.

$$\lambda(x) = \int_{-\infty}^{\infty}\int_{-\infty}^{\infty} W_{\sigma_s}(\xi-x)W_{\sigma_r}(I(\xi)-I(x))d\xi \quad (14)$$

Where $I(x)$ and $h(x)$ denote input images and output images, respectively. And $W_{\sigma_s}$ measures the geometric closeness between the neighborhood center x and a nearby point $\xi$ and $W_{\sigma_r}$ measures the photometric similarity between the pixel at the neighborhood center x and that of a nearby point $\xi$. Thus, the similarity function $W_{\sigma_r}$ operates in the range of the image function I, while the closeness function $W_{\sigma_s}$ operates in the domain of I.

Figure 7:
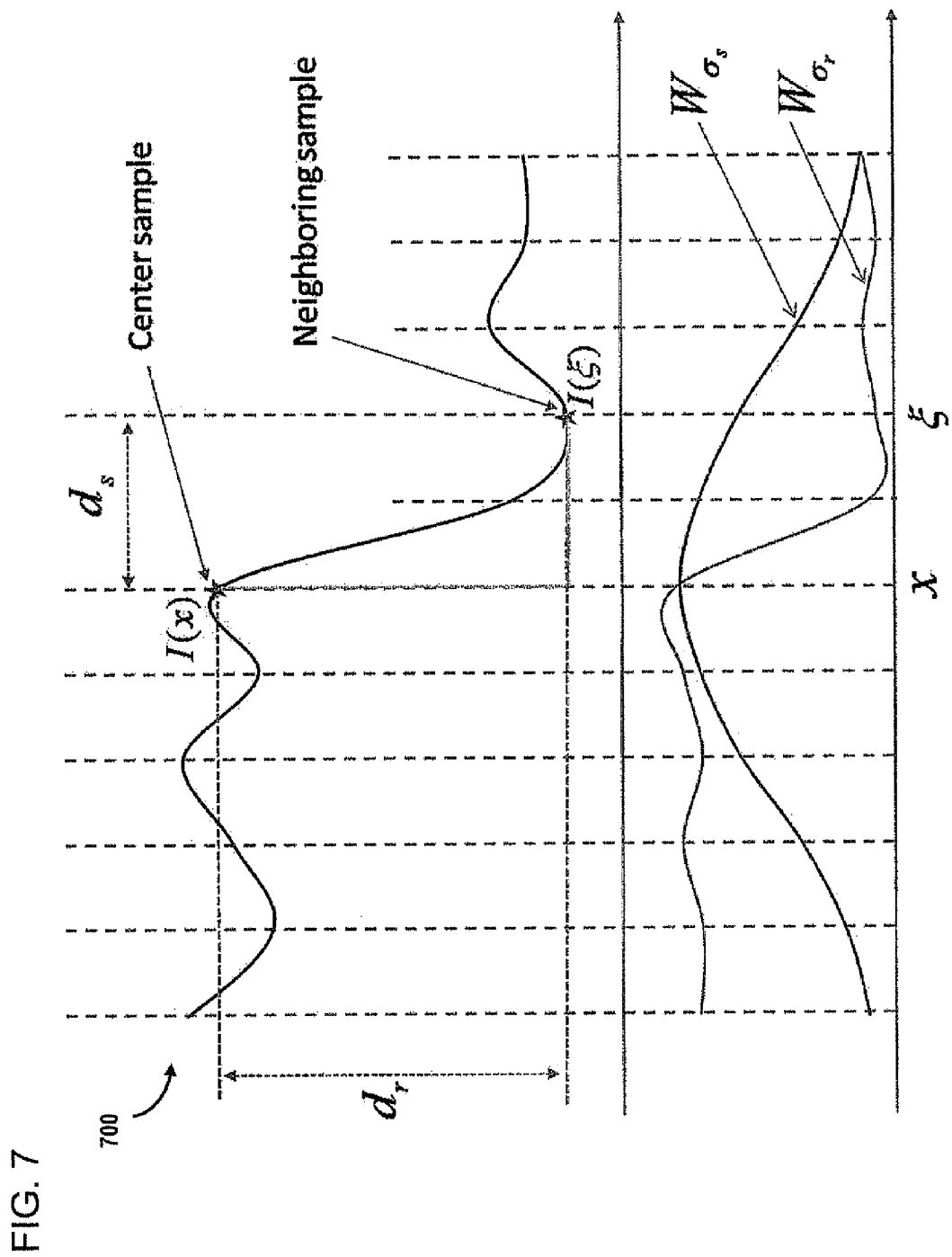
FIG. 7 illustrates an example of a scheme diagram of a bilateral filter.

FIG. 7 illustrates an example of a scheme diagram 700 of a bilateral filter. As shown in the FIG. 7, the bilateral filter may replace the pixel value at x with an average of similar and nearby pixel values. In smooth regions, pixel values in a small neighborhood may be similar to each other, and the bilateral filter acts essentially as a standard domain filter, averaging away the small, weakly correlated differences between pixel values caused by noise. This scheme is further described in Elad, 2002, Image Processing, IEEE Transactions, 11(10), 1141-1151, which is incorporated by reference in its entirety.

The bilateral filtering may be performed by many different kernels. In some embodiments the bilateral filtering may be performed by a Gaussian filtering. The Gaussian filtering may be shift-invariant Gaussian filtering, in which both the spatial function $W_{\sigma_s}$ and the range function $W_{\sigma_r}$ are Gaussian functions of the Euclidean distance between their arguments. More specifically, $W_{\sigma_s}$ may be described as:

$$W_{\sigma_s}(\xi-x) = e^{-\frac{1}{2}[d_s^2/\sigma_s^2]} \quad (15)$$

where $d_s=\|\xi-x\|$ is the Euclidean distance. The range function $W_{\sigma_r}$ may be perfectly analogous to $W_{\sigma_s}$:

$$W_{\sigma_r}(\xi-x) = e^{-\frac{1}{2}[d_r^2/\sigma_r^2]} \quad (16)$$

where $d_r=|I(\xi)-I(x)|$ is a suitable measure of distance in intensity space.

In the scalar case, this may be simply the absolute difference of the pixel difference. The Gaussian range filter may also be insensitive to overall additive changes of image intensity. Thus, the range filter may also be shift-invariant.

As discussed above, FIG. 6 illustrates a multiscale bilateral composition. The decomposing method may further include an obtaining step 135 that obtains each image (sinogram) that is filtered. In further embodiments, the method may further include a determination step 135 that determines whether the filtering step should be repeated so as to build a series of filtered images having different scales as shown in step 136. The filtering step may be repeated until the number of images at the predetermined scale N is obtained.

In some embodiments, a series of filtered images $I^i$ that preserve the strongest edges in I while smoothing small changes in intensity may be obtained based with the following calculations.

For the calculations, it is assumed that the original image obtained in step 131 is the $0^{th}$ scale (i=0), that is, set $I^0=I$. The image is then filtered through a bilateral filter in steps 132 and 133. Application of the bilateral filter may compute the following:

$$I_n^{i+1} = \frac{1}{\lambda}\sum_{k\in\Omega} W_{\sigma_s,i}(k)\cdot W_{\sigma_r,i}(I_{n+k}^i - I_n^i)\cdot I_{n+k}^i \quad (17)$$

with $$\lambda = \sum_{k\in\Omega} W_{\sigma_s,i}(k)\cdot W_{\sigma_r,i}(I_{n+k}^i - I_n^i)$$

where n is a pixel coordinate, $W_\sigma(x)=\exp(-x^2/\sigma^2)$, $\sigma_{s,i}$ and $\sigma_{r,i}$ are the widths of the spatial and range Gaussians respectively and k is an offset relative to n that runs across the support of the spatial Gaussian. The repeated convolution by $W_{\sigma_s,i}$ may increase the spatial smoothing at each scale i. At the finest scale, the spatial kernel may be set to $\sigma_{s,i}=2^{i-1}\sigma_s$ (i>0). However, because the bilateral filter is non-linear, the filtered image $I^i$ may not be identical to bilaterally filtering the original input image I with a spatial kernel of cumulative width. The range Gaussian $W_{\sigma_r,i}$ is an edge-stopping function.

In some embodiments, in order to preserve the edge after several iterations of the bilateral decomposition, $\sigma_{r,i}=2^{i-1}\sigma_r$ may be set. Increasing the width of the range Gaussian $W_{\sigma_r,i}$ by a factor of 2 at every scale may increase the chance that an unwanted edge that survives at previous iteration may be smoothed away in later iterations. Also, the initial width $\sigma_r$ may be set to A/25, where A is the intensity range of the image.

Figure 8:
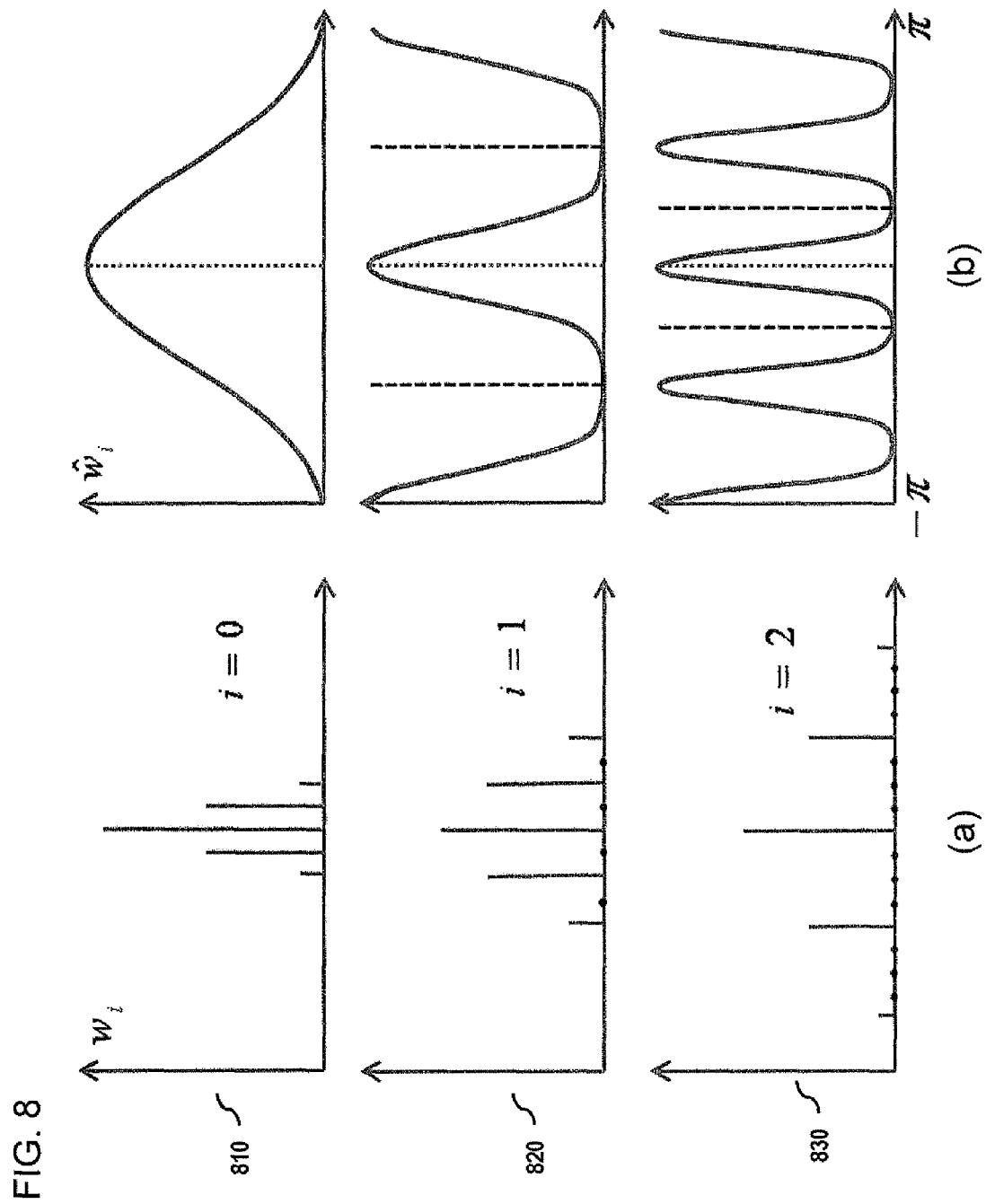
FIGS. 8(a) and 8(b) illustrate an example of three scales of generating kernel $w_i$, and its Fourier transforms $\hat{w}_i$.

FIGS. 8(a) and 8(b) illustrate an example of three scales 810, 820, and 830 of generating kernel $W_i$ and its Fourier transforms $\hat{w}_i$. Dashed lines in FIG. 8(a) show the envelopes of three scales kernel. Dashed lines in FIG. 8(b) indicate smoothing condition boundaries $\pi/2^{i-1}>|\omega|>\pi/2^i$.

As shown in FIGS. 8(a) and 8(b), $w_i$ denotes $W_{\sigma_r,i}$ and $W_{\sigma_s,i}$. These generating kernels $w^i$ have a fixed number $2m+1$, of non-zero coefficients, yet expand in space by the introduction of $2^i-1$ zeros between these coefficients. The expansion of the $w^i$ by inserting zeros leads to the introduction of $2^i$ aliases in $\hat{w}^i(\omega)$. Thus, the generating kernels themselves do not operate as low-pass filters. However, as long as the following smoothing condition, $\hat{w}^i(\omega)<\epsilon$ for $\pi/2^{i-1}>|\omega|>\pi/2^i$ holds, it will follow that $\hat{w}^i(\omega)<\epsilon$ for $|\omega|>\pi/2^i$ and $\hat{w}^i$ may be essentially a low-pass filter.

Figure 9:
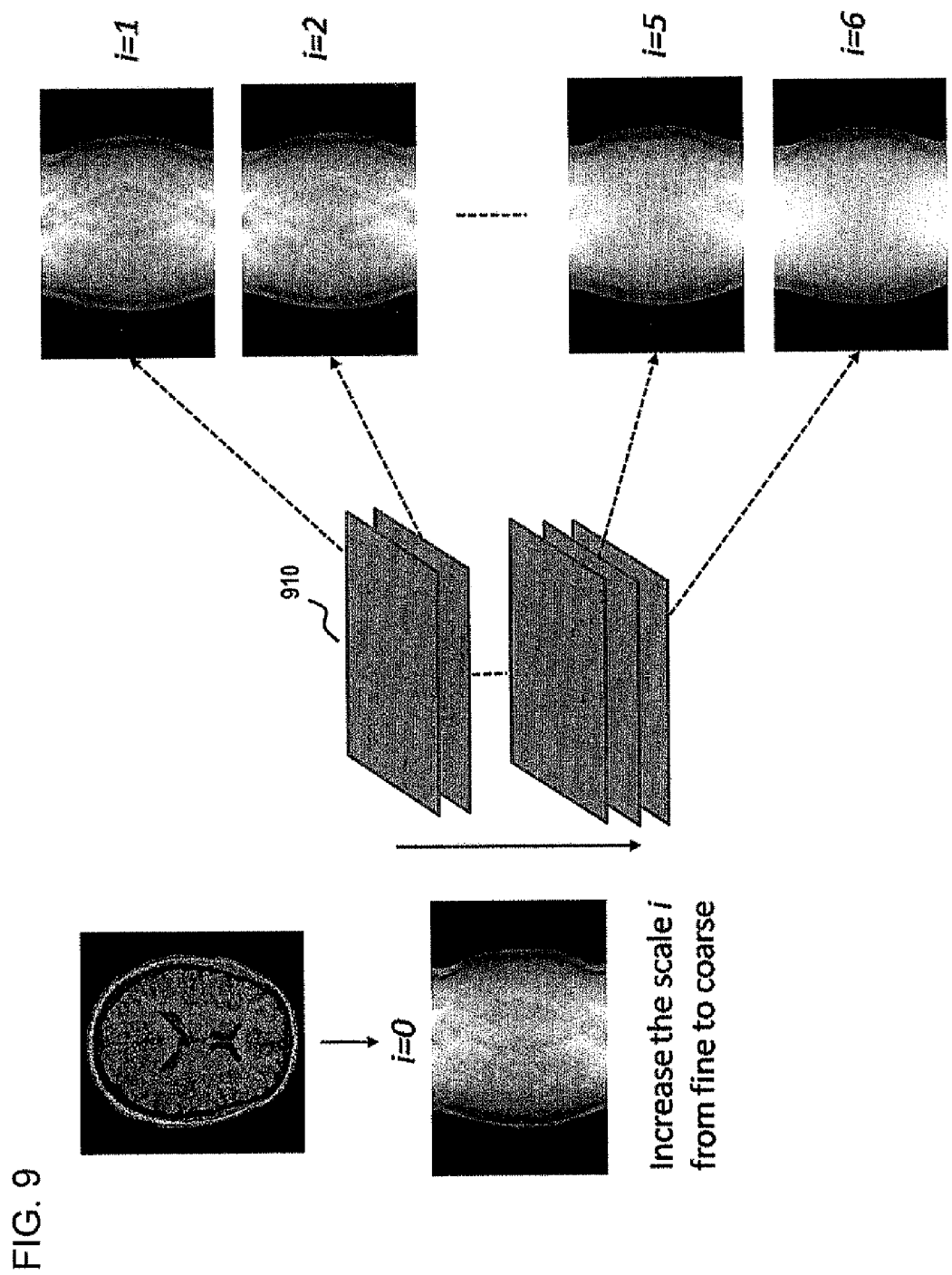
FIG. 9 illustrates a scale-space of decomposed images constructed by bilateral filtering.

FIG. 9 illustrates a scale-space 910 constructed by bilateral filtering. The scale space 910 is composed of a stack of images filtered at different scales where i=0 is the original image. FIG. 9 illustrates six scales (i=6), however, it would be understood that the decomposing step may be performed to any number of scales. The scale number may be selected based on the anatomy selected to be scanned.

As shown in FIG. 9, the multiscale bilateral decomposition technique smoothes the images as the scale i increases. The scale i may be considered as the scale level and the original image is at the level 0. When the scale increases, the images become more blurred and contain more general information. Unlike many multi-resolution techniques where the images are down-sampled along the resolution, it is not necessary to subsample the $I^i$ because such downsampling may blur the edges in $I^i$. In addition, downsampling may prevent the decomposition from being translation invariant and could introduce grid artifacts when the coarser scales are manipulated.

Figure 10:
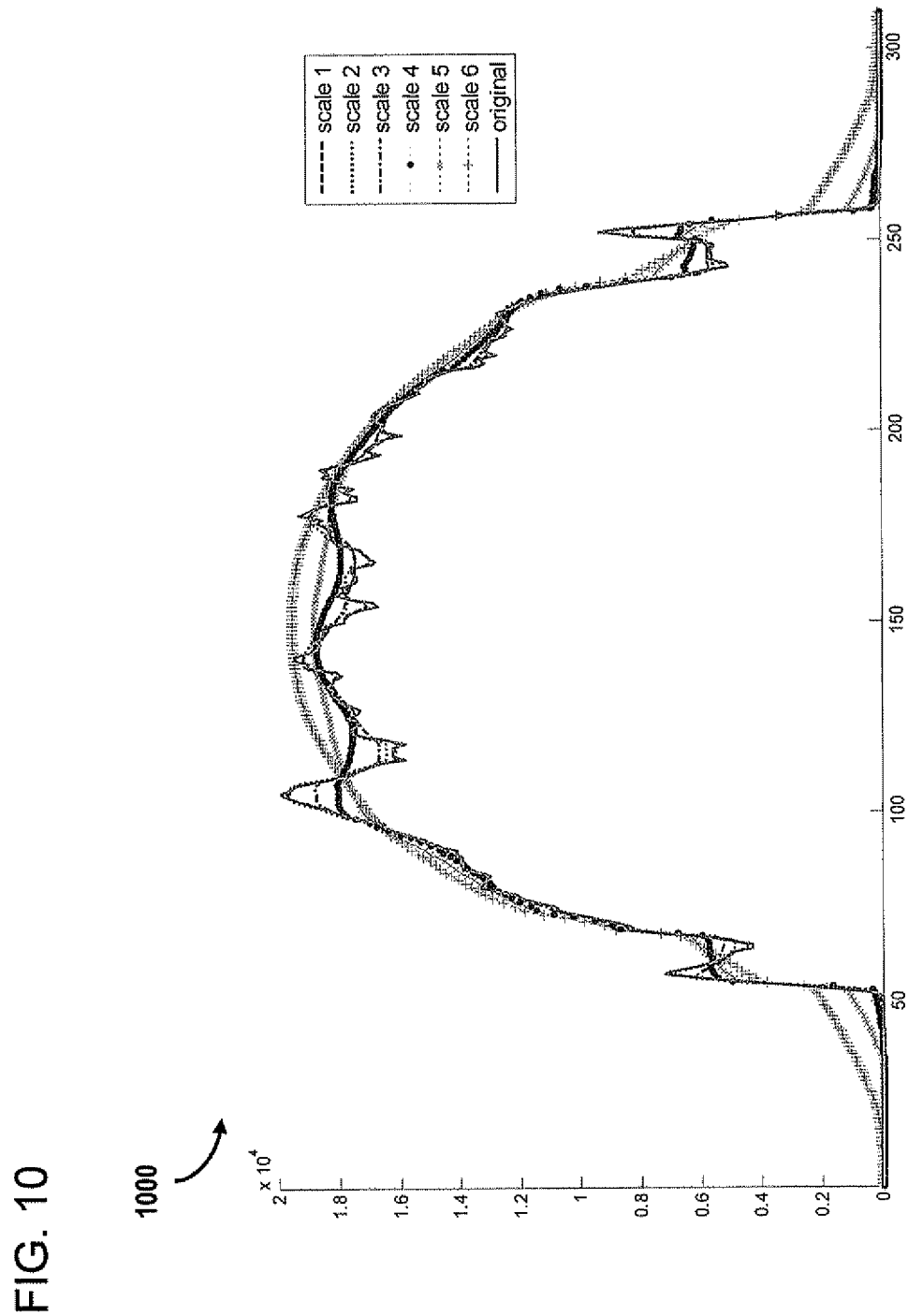
FIG. 10 illustrates a comparison of the profiles of the decomposed images in every scale.

FIG. 10 illustrates a comparison of the profiles 1000 in every scale. As shown in FIG. 10, when the scale increases, small edges in intra-region are smoothed and the big edges in the inter-region are preserved.

Gradient Filtering

After the sinogram is decomposed into a multiscale sinogram, the segmentation method 100 may further include a filtering step 140 that filters each sinogram through a predetermined gradient filter, as shown in FIG. 1.

In some embodiments, the images may be filtered through different filters. In some embodiments, the images may be use two sets of filters. In further embodiments, the filters may be selected based on the anatomy scanned. FIGS. 11(a) and 11(b) show kernels 1110 and 1120, respectively, for two filters utilized for a brain scan.

Morphological Image Processing

In further embodiments, the method 100 may optionally include a processing step 150 for processing each sinogram with morphological image processing.

Combining Filtered Sinograms through Reconstruction of Sinogram

In further embodiments, after each sinogram is filtered and processed, the sinograms may be combined in step 160. The combined sinograms may determine a binary sinogram in step 170. In some embodiments, a thresholding method is used to determine the binary sinogram from the combined sinograms. The binary sinogram may then be used to reconstruct the sinogram in step 180. In some embodiments, the reconstruction step 180 may include transforming the sinogram from the Radon Domain to the Image Domain. The transformation may be based on any known calculations. In some embodiments, the reconstruction may be performed using filter back projection or ordered-subset expectation maximization (OSEM) methods.

Figure 12:
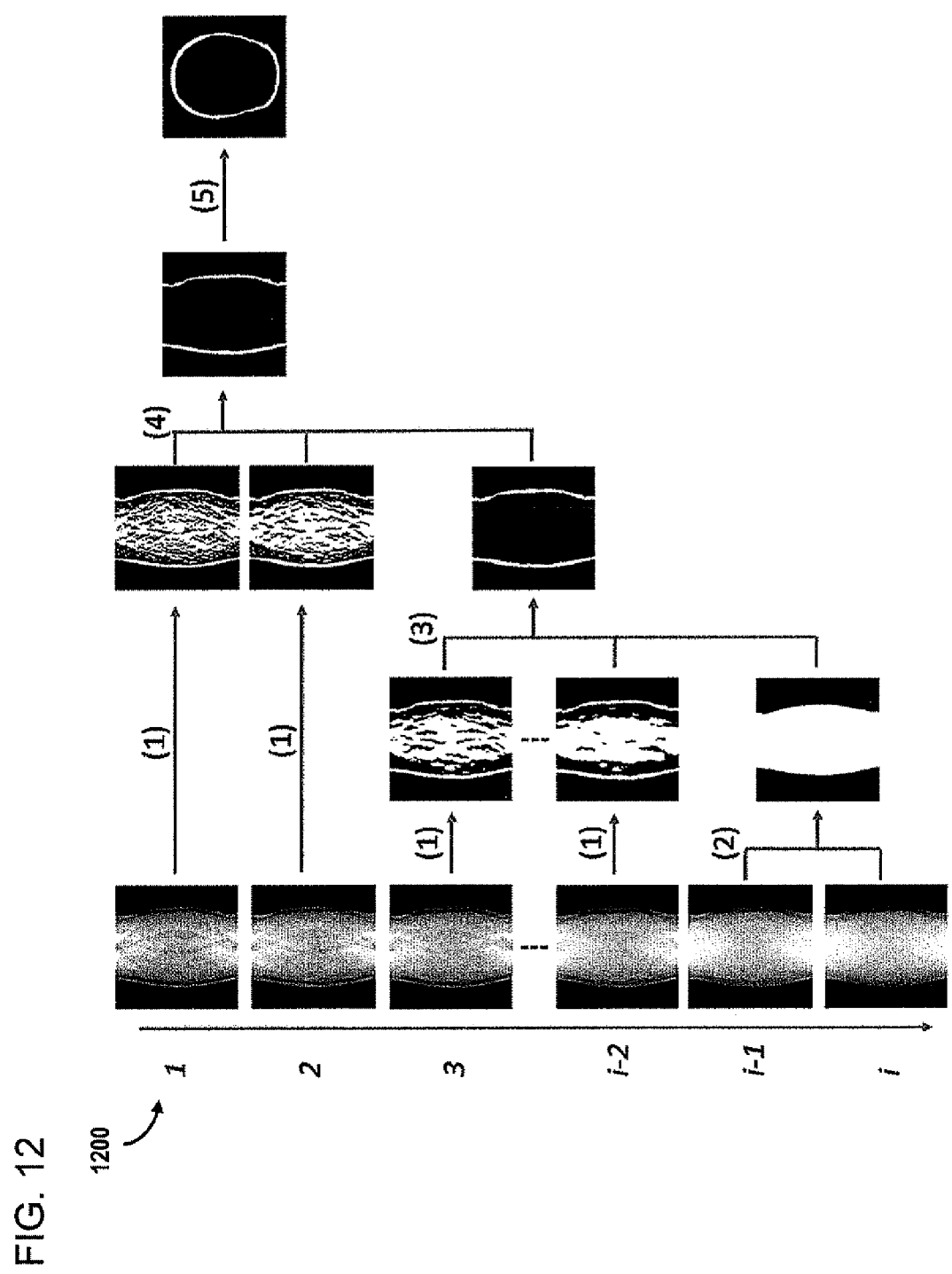
FIG. 12 illustrates multiscale processing of a brain image to obtain a reconstructed sinogram according to an exemplary embodiment.

FIG. 12 is an illustration of multiscale processing 1200 performed in steps 160 through 180 on a brain image to obtain a reconstructed sinogram. The scale increases from up to down. After the filtered images are processed, the upper half of the first filtered mage is combined with the lower half of the second filtered image in order to get a new sinogram as shown in (1) of FIG. 10. These images are then used to get a mask in step (2). From the mask obtained in step (2), the mask is inversed to obtain the mask in step (3). After which, the mask from step (3) may be used to obtain a binary skull in the Radon domain in step (4). The skull then may be reconstructed in step (5) to obtain the segmented skull Reconstruction in step 180, may be performed after obtaining the binary sinogram as discussed above. In some embodiments, a threshold may be utilized in the reconstruction to eliminate some artifacts introduced by reconstruction. Reconstruction may be described as:

$$f(x,y)=\int_0^\pi Q_\theta(x\cos\theta+y\sin\theta)d\theta \qquad (18)$$

With $Q_\theta$ are the ramp-filtered projections.

After the reconstruction, in some embodiments, the segmented tissue may be displayed in step 190. In other embodiments, the segmented MR Image with segmented tissue may be forwarded for further processing. In some embodiments, the segmented MR Image may be used as part of the attenuation control of PET images. In further embodiments, the segmented MR Image with segmented tissue may be both displayed and forwarded.

System Implementation

Figure 13:
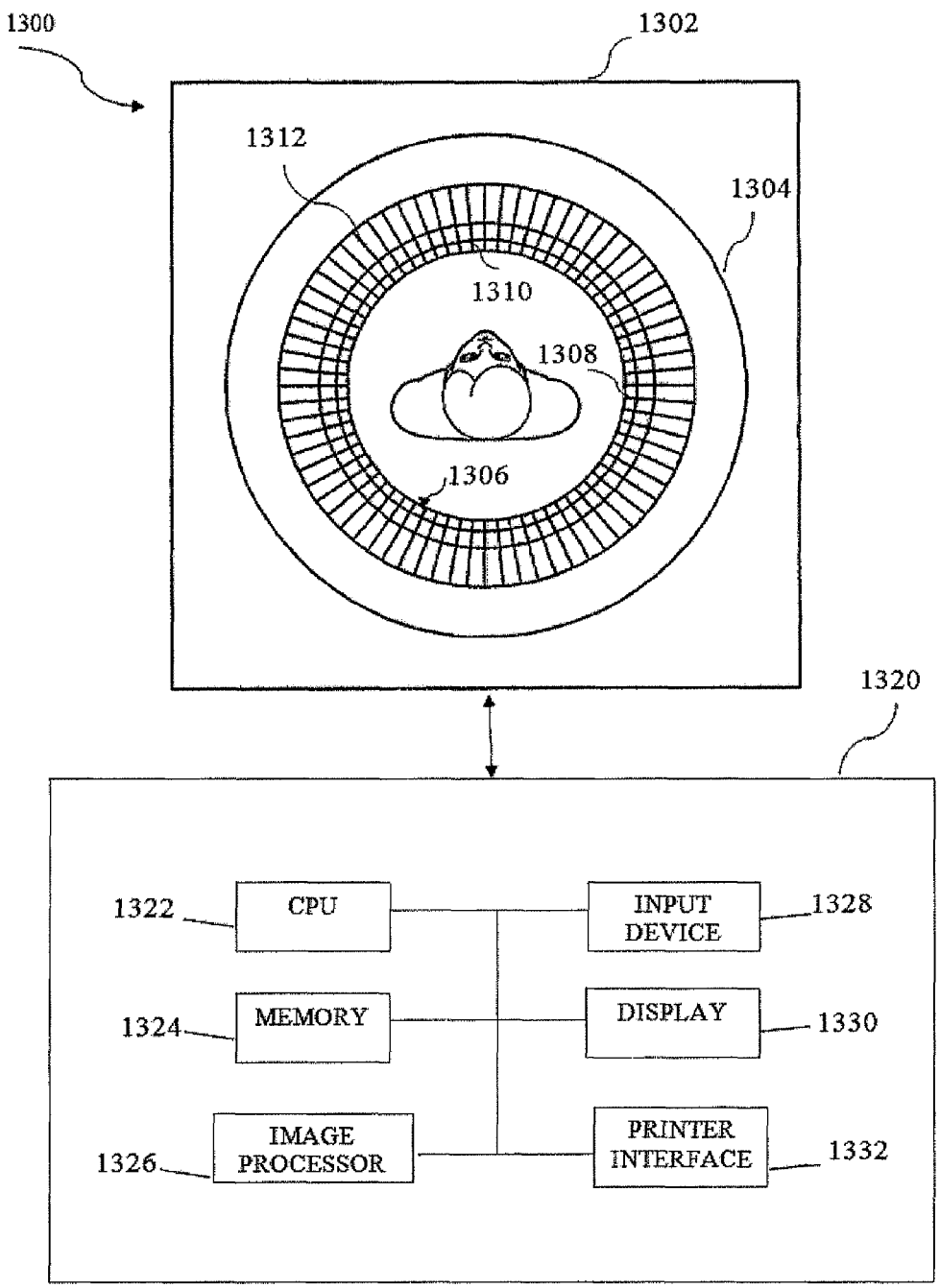
FIG. 13 shows an example of an apparatus for providing superposed MR and PET imaging according to an exemplary embodiment.

FIG. 13 shows an example of a known apparatus 1300 for superposed MR and PET imaging. The apparatus 1300 may include any known MRI tube 102. The MRI tube 1304 defines a longitudinal direction z, which extends orthogonally to the plane of the drawing of FIG. 13. Although not shown, the system may contain a scanner including one or more gamma ray detectors (not shown) (e.g., a ring of gamma ray detectors) incorporated into a RF coil assembly (not shown). The one or more gamma ray detectors may be configured to detect gamma rays from positron annihilations and may include a plurality of scintillators and photodetectors arranged circumferentially about a gantry (i.e., a ring of gamma ray detectors or a detector ring).

As shown in FIG. 13, the system may further include a plurality of PET detection units 1306 arranged in mutually opposing pairs around the longitudinal direction z are arranged coaxially within the MRI tube 1304. The PET detection units 1306 may preferably include a photodiode array 1310, such an APD photodiode array, with an upstream array of crystals 1308, such as LSO crystals, and an electrical amplifier circuit (AMP) 1306.

The apparatus may further include a computer system 1320 to carry out the image processing for superposed MR and PET imaging. The computer system 1320 may further be used to control the operation of the system or a separate system may be included.

The computer system 1320 may include a number of modules that communicate with each other through electrical and/or data connections (not shown). Data connections may be direct wired links or may be fiber optic connections or wireless communications links or the like. The computer system 1320 may also be connected to permanent or back-up memory storage, a network, or may communicate with a separate system control through a link (not shown). The modules may include a CPU 1322, a memory 1324, an image processor 1326, an input device 1328, a display 1330, and a printer interface 1332. The computer system 1320 may also be connected to another computer system as well as a network.

The CPU 1322 may be one or more of any known central processing unit, including but not limited to a processor, or a microprocessor. The CPU 1322 may be coupled directly or indirectly to memory elements. The memory 1324 may include random access memory (RAM), read only memory (ROM), disk drive, tape drive, etc., or a combinations thereof). The memory may also include a frame buffer for storing image data arrays.

The described processes (e.g., FIGS. 1 and 6) may be implemented as a routine that is stored in memory 1324 and executed by the CPU 1322. As such, the computer system 1320 may be a general purpose computer system that becomes a specific purpose computer system when executing the routine of the disclosure. The computer system 1320 may also include an operating system and micro instruction code. The various processes and functions described herein may either be part of the micro instruction code or part of the application program or routine (or combination thereof) that is executed via the operating system. In addition, various other peripheral devices may be connected to the computer platform such as an additional data storage device, a printing device. and I/O devices.

The image processor 1326 may be one or more of any known central processing unit, including but not limited to a processor, or a microprocessor. In some embodiments, the image processor 1326 also processes the data. In other embodiments, the image processor 1326 may be replaced by image processing functionality on the CPU 1322.

The input device 1328 may include a mouse, joystick, keyboard, track ball, touch activated screen, light wand, voice control, or any similar or equivalent input device, and may be used for interactive geometry prescription. The input device 1328 may control the production, display of images on the display 1330, and printing of the images by the printer interface 1332. The display 1330 and the printer interface 1332 may be any known display screen and the printer interface 1332 may be any known printer, either locally or network connected.

An MRI scan is complete when one or more sets of raw k-space data has been acquired in by the image processor 1326. The image processor 1326 reconstructs the raw k-space data by transforming the data raw k-space data (via Fourier transformation or another technique) into image data. This image data may then be stored in the memory 1324. In other embodiments, another computer system may assume the duties of image reconstruction or other functions of the image processor 1326. In response to commands received from the input device 1328, the image data stored in the memory 1324 may be archived in long term storage or may be further processed by the image processor 1326 and presented on the display 1330. PET images may be reconstructed by the image processor 1326 and may be combined with MR images to produce hybrid structural and metabolic or functional images.

It is to be understood that the embodiments of the disclosure be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method, performed by a computer having a memory and a processor, for segmenting an anatomical landmark in digital medical images, comprising:

transforming at least one digital image of an anatomical landmark from an Image Domain to a Radon Domain to obtain an original sinogram, the transforming being based on a calculation as follows $P_s(\alpha)=Rf(\alpha,s)=\int_{-\infty}^{\infty}\int_{-\infty}^{\infty}f(x,y)\delta(s-x\cos\alpha-y\sin\alpha)dxdy$ $\alpha\epsilon[0,\pi]s\epsilon R$;

decomposing the original sinogram to obtain a plurality of sinograms, each of the plurality of sinograms being at a different scale;

combining the plurality of sinograms into a binary sinogram; and reconstructing the binary sinogram into a reconstructed sinogram.

2. The method according to claim 1, wherein the reconstructing includes transforming the binary sinogram from the Radon Domain to the Image Domain to obtain a segmented magnetic resonance (MR) Image.

3. The method according to claim 2, further comprising: displaying the segmented MR Image.

4. The method according to claim 2, further comprising: using the segmented MR Image for attenuation control of a positron emission tomography (PET) Image.

5. The method according to claim 1, wherein the decomposing is performed using a bilateral filter.

6. The method according to claim 1, wherein the decomposing includes filtering the original sinogram to a scale of six, wherein the plurality of sinograms is six sinograms.

7. The method according to claim 1, further comprising: filtering each of the plurality of sinograms with a gradient filter after the decomposing of the original sinogram.

8. The method according to claim 7, wherein the gradient filter is selected based on the anatomical landmark.

9. The method according to claim 1, wherein the anatomical landmark includes any one of a brain, a lung, or a thorax.

10. A non-transitory computer-readable storage medium storing instructions for segmenting an anatomical landmark in digital medical images, the instructions comprising:

transforming at least one digital image of an anatomical landmark from an Image Domain to a Radon Domain to obtain an original sinogram, the transforming being based on a calculation as follows $P_s(\alpha)=Rf(\alpha,s)=\int_{-\infty}^{\infty}\int_{-\infty}^{\infty}f(x,y)\delta(s-x\cos\alpha-y\sin\alpha)dxdy$ $\alpha\epsilon[0,\pi]s\epsilon R$;

decomposing the original sinogram to obtain a plurality of sinograms, each of the plurality of sinograms being at a different scale;

combining the plurality of sinograms into a binary sinogram; and reconstructing the binary sinogram into a reconstructed sinogram.

11. The medium according to claim 10, wherein the reconstructing includes transforming the binary sinogram from the Radon Domain to the Image Domain to obtain a segmented magnetic resonance (MR) Image.

12. The medium according to claim 11, further comprising: displaying the segmented MR Image.

13. The medium according to claim 11, further comprising: using the segmented MR Image for attenuation control of a positron emission tomography (PET) Image.

14. The medium according to claim 10, wherein the decomposing is performed using a bilateral filter.

15. The medium according to claim 10, wherein the filtering includes filtering the original sinogram to a scale of six, wherein the plurality of sinograms is six sinograms.

16. The medium according to claim 10, further comprising: filtering each of the plurality of sinograms with a gradient filter after the decomposing of the original sinogram.

17. The medium according to claim 10, wherein the gradient filter is selected based on the anatomical landmark.

18. The medium according to claim 10, wherein the anatomical landmark includes any one of a brain, at least one lung, a thorax, or at least one bone.

19. A system for processing positron emission tomography (PET) and magnetic resonance (MR) images from a PET/MRI machine, comprising:

an apparatus including:

at least one processor; and at least one memory including computer program code, wherein the at least one memory and the computer program code are configured to, with the at least one processor, cause the apparatus to perform at least the following:

transforming at least one digital image of an anatomical landmark from an Image Domain to a Radon Domain to obtain an original sinogram, the transforming being based on a calculation as follows $P_s(\alpha)=Rf(\alpha,s)=\int_{-\infty}^{\infty}\int_{-\infty}^{\infty}f(x,y)\delta(s-x\cos\alpha-y\sin\alpha)dxdy$ $\alpha\epsilon[0,\pi]$ $s\epsilon R$;

decomposing the original sinogram to obtain a plurality of sinograms, each of the plurality of sinograms being at a different scale;

combining the plurality of sinograms into a binary sinogram; and reconstructing the binary sinogram into a reconstructed sinogram.

* * * * *